United States Patent [19]

Chapelon et al.

[11] Patent Number: 5,474,071
[45] Date of Patent: Dec. 12, 1995

[54] THERAPEUTIC ENDO-RECTAL PROBE AND APPARATUS CONSTITUTING AN APPLICATION THEREOF FOR DESTROYING CANCER TISSUE, IN PARTICULAR OF THE PROSTATE, AND PREFERABLY IN COMBINATION WITH AN IMAGING ENDO-CAVITARY-PROBE

[75] Inventors: Jean Y. Chapelon, Villeurbanne; Dominique Cathignol, Genas; Albert Gelet, Lyons; Emmanuel Blanc, Saint Genis Laval, all of France

[73] Assignees: Technomed Medical Systems, Vaulx-en-Velin; Iserm-Institut National de la Sante et de la Recherche Medicale, Paris Cedex, both of France

[21] Appl. No.: 200,877

[22] Filed: Feb. 22, 1994

Related U.S. Application Data

[63] Continuation of Ser. No. 795,197, Nov. 19, 1991, abandoned.

[30] Foreign Application Priority Data

| Mar. 5, 1991 | [FR] | France | 91 02620 |
| Jul. 19, 1991 | [FR] | France | 91 09197 |

[51] Int. Cl.$^6$ .................................................... A61B 8/12
[52] U.S. Cl. .................. 128/660.03; 128/662.06; 128/662.03; 607/97; 601/3
[58] Field of Search ............ 128/653.1, 660.03, 128/660.01, 660.02, 662.03, 662.06; 604/22; 606/128; 607/2, 4, 105, 97; 601/3

[56] References Cited

U.S. PATENT DOCUMENTS

| 4,605,009 | 8/1986 | Pourcelot et al. | 128/662.006 |
| 4,823,812 | 4/1989 | Eshel et al. | 128/804 |
| 4,841,979 | 6/1989 | Dow et al. | 128/660.001 |
| 4,972,839 | 11/1990 | Angelsen | 128/662.006 |
| 5,003,991 | 4/1991 | Takayama et al. | 128/401 |
| 5,036,855 | 8/1991 | Fry et al. | 128/660.03 |
| 5,115,814 | 5/1992 | Griffith et al. | 128/660.03 X |
| 5,176,142 | 1/1993 | Mason | 128/662.06 |
| 5,178,150 | 1/1993 | Silverstein et al. | 128/662.06 |
| 5,181,514 | 1/1993 | Solomon et al. | 128/662.06 X |

FOREIGN PATENT DOCUMENTS

| 0139607 | 2/1985 | European Pat. Off. | A61N 1/40 |
| 0137529 | 4/1985 | European Pat. Off. | G10K 11/34 |
| 0326701 | 8/1989 | European Pat. Off. | A61B 17/22 |
| 0363239 | 9/1989 | European Pat. Off. | A61B 17/22 |
| 0370890 | 5/1990 | European Pat. Off. | |
| 8225920 U | 5/1985 | Germany | A61B 8/12 |
| 3726210 | 2/1988 | Germany | 606/128 |
| 3813975A1 | 9/1989 | Germany | A61B 17/36 |
| 3813975 | 11/1989 | Germany | 128/660.003 |
| WO89/07909 | 8/1989 | WIPO | A61B 8/00 |

OTHER PUBLICATIONS

John B. Pond "The Role of Heat in the Production of Ultrasonic Focal Lesions" Jan. 3, 1969, pp. 1607–1611.
Helmuth Schultz–Haakh et al., "Ultrasonic Treatment of Varicose Veins", pp. 129–137.
Frederic L. Lizzi et al., "Ultrasonic Hyperthermia For Ophthalmic Theraphy", IEEE Transactions on Sonics and Ultrasonics, vol. SU–31, No. 5, Sep., 1984, pp. 473–481.
IEEE 1989 Ultrasonics Symposium, Oct. 3–6, 1989 pp. 755–766.
F. J. Fry et al., "Threshold Ultrasonic Dosages for Structural Changes in the Mammalian Brain", The Journal of The Acoustical Society of America, May 6, 1970.

*Primary Examiner*—George Manuel
*Assistant Examiner*—Brian L. Casler
*Attorney, Agent, or Firm*—Cohen, Pontani, Lieberman, Pavane

[57] ABSTRACT

A therapeutic endo-rectal probe comprises a piezoelectric transducer element mounted in a support member itself connected to a rigid guide means enabling endo-rectal insertion of the probe, the outside shape of the support member preferably being that of a disk having an outline that is for the most part substantially circular or substantially elliptical, thereby facilitating endo-rectal insertion.

69 Claims, 7 Drawing Sheets

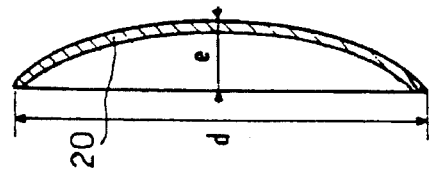
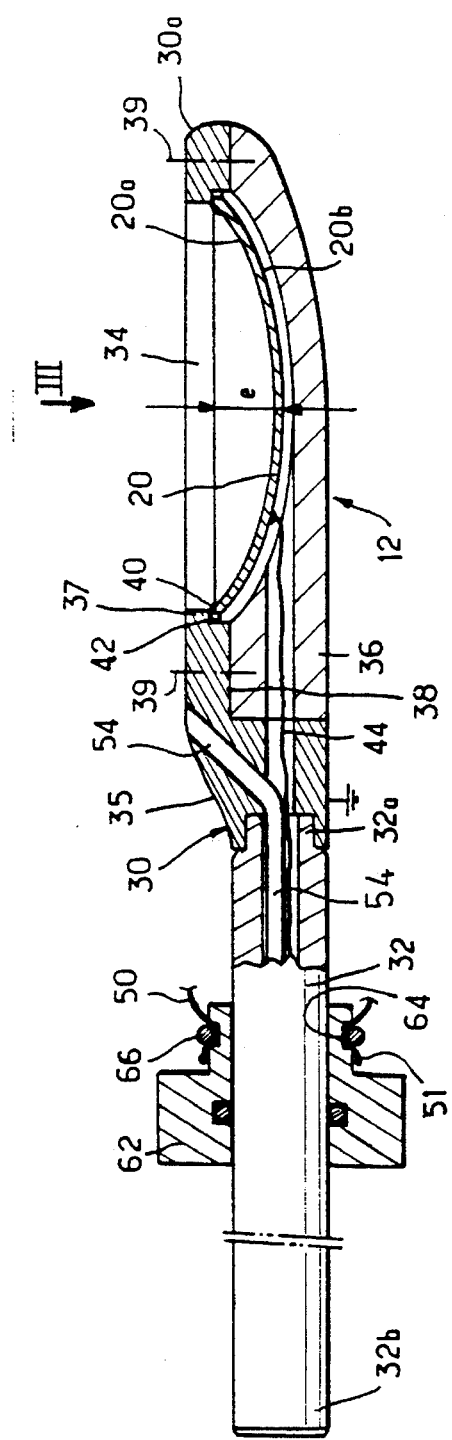
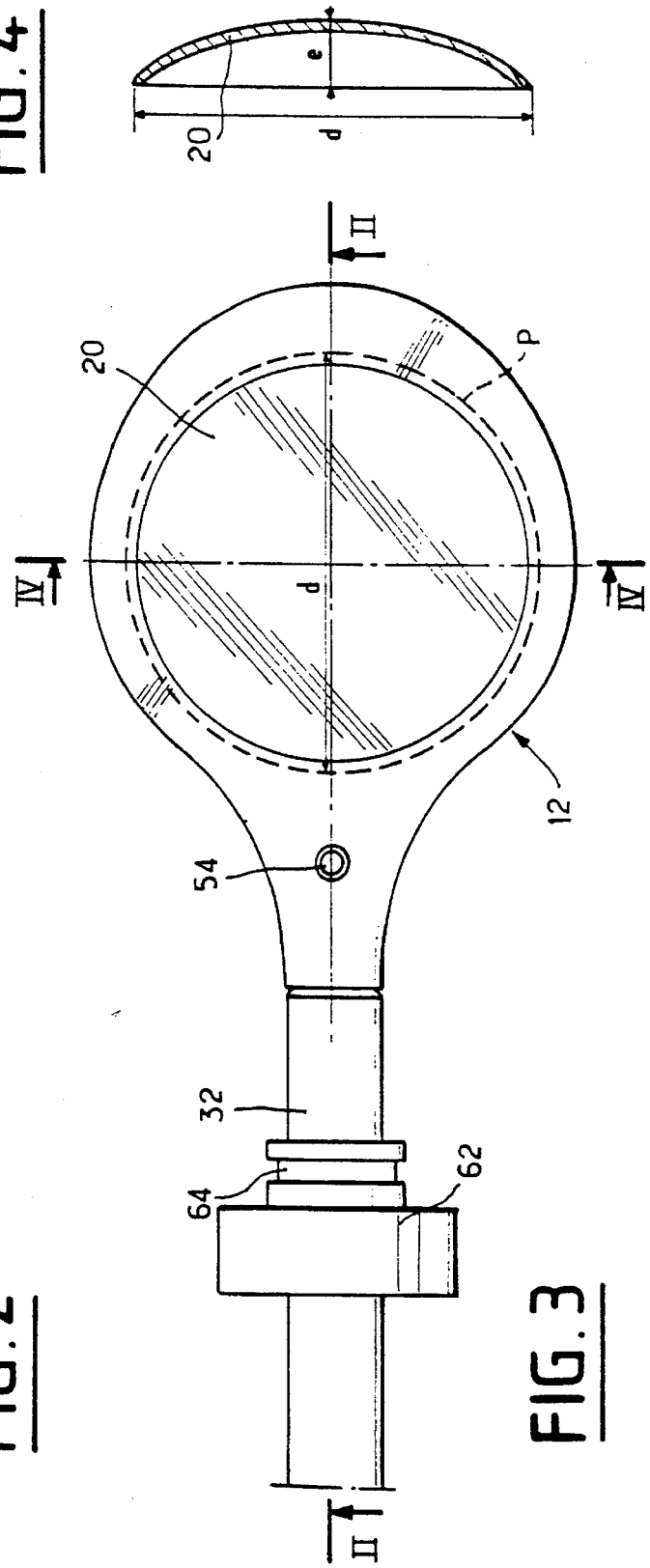

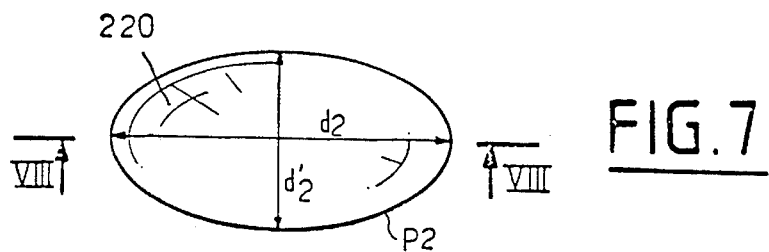
FIG.7
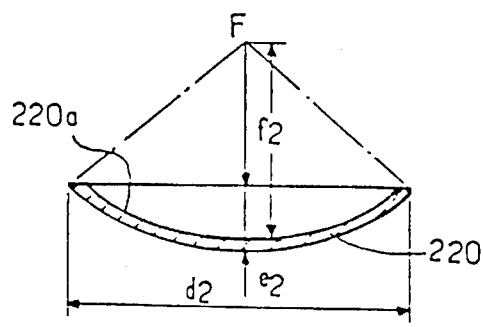
FIG.8
FIG.9
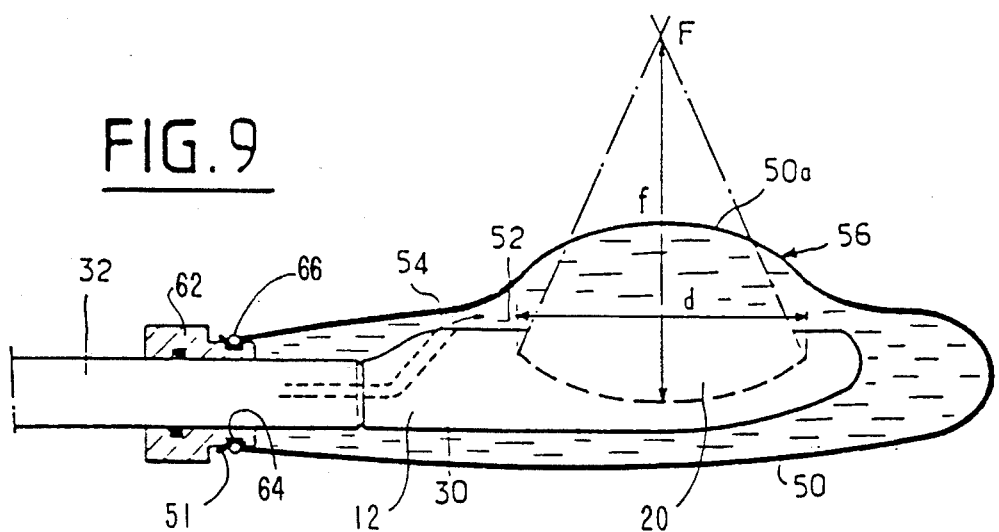
FIG.10
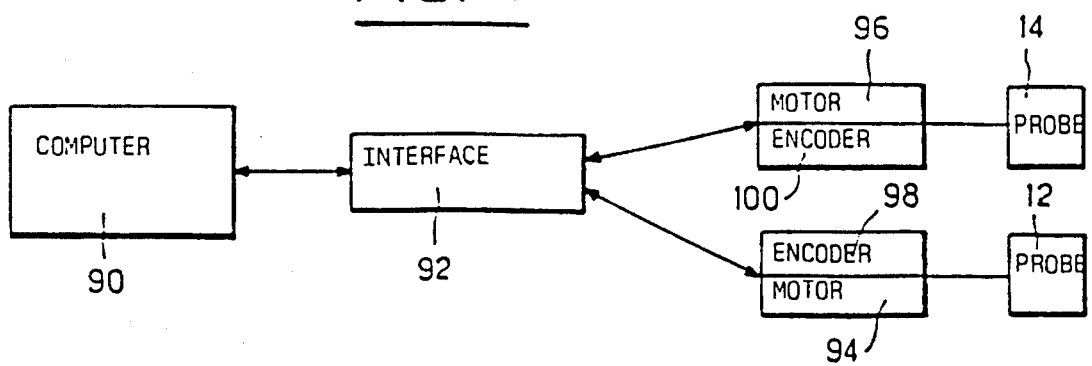

THERAPEUTIC ENDO-RECTAL PROBE AND APPARATUS CONSTITUTING AN APPLICATION THEREOF FOR DESTROYING CANCER TISSUE, IN PARTICULAR OF THE PROSTATE, AND PREFERABLY IN COMBINATION WITH AN IMAGING ENDO-CAVITARY-PROBE

This is a continuation of U.S. application Ser. No. 07/795,197, filed Nov. 19, 1991 now abandoned.

The present invention relates essentially to a therapeutic endo-rectal probe, and also to apparatus constituting an application thereof for destroying tumor tissue, in particular of the prostate, and preferably in combination with an imaging endo-cavitary probe. Tumor tissue, in particular of the prostate, is preferably destroyed by the action of ultrasonic soundwaves that are pulsed and focused.

BACKGROUND OF THE INVENTION

It is already known that tissue can be destroyed by being subjected to a given "heat dose". At a given temperature, the heat dose is a function of the length of time that heat is applied.

Various means have been proposed for raising temperature, in particular by using infrared radiation or microwave radiation, (see Biodan's U.S. Pat. No. 4,823,812, inventor Eshel).

When using these methods, it is not possible to cause selective heating of the tissue insofar as the radiation is omnidirectional and cannot be focused on a target zone. In addition, these methods are not adapted or are poorly adapted to treating zones of deep tissue. (See the article by Fry entitled "Threshold ultrasonic dosage for structural changes in mammalian brain" published in JASA (1970, 48, 1413–1417)).

To solve this problem, in IEEE Transactions on sonics and ultrasonics, Vol. SE-31, No. 5, September 1984, pp. 473–480, Lizzi et al. propose using soundwaves that are focused to obtain tissue-destroying hyperthermia. As a result, soundwaves of sufficient energy when applied for a sufficiently long period of time serve to reach a "heat dose" threshold required for destroying the target tissue.

The Document WO 89/07909 also describes an apparatus for locating and destroying tumors by ultrasonic hyperthermia.

An apparatus is also known from Document EP-A-0 363 239 for localized destruction of soft structures by means of focused negative elastic pressure waves suitable for giving rise to a cavitation phenomenon in the tissue subjected to the sound. The cavitation phenomenon has the effect of giving rise to localized large mechanical stresses at the cavitation location, thereby destroying the tissue concerned.

When using soundwaves, tissue is generally destroyed by a combination of the cavitation effect and of the heating effect. Unfortunately, the three-dimensional position of where cavitation takes place is difficult to control because cavitation takes place preferentially at the various interfaces encountered by the soundwaves, such as those associated with the skin, with various organs, or with blood vessels. For example, when applying treatment from outside the body as described in EP-A-0 363 239, there is a danger of cavitation phenomena arising anywhere along the path followed by the wave propagating between the transducer and the zone of focus. Given that such cavitation phenomena are destructive, it becomes difficult to control the therapy and to limit it to the target zone.

In addition, the presence of cavitation bubbles on the path of the soundwaves gives rise to a sound screen such that the treatment loses some of its efficiency.

It can thus be seen that it is highly advantageous to minimize the path followed by the sound to reach the focus zone, thus reducing the number of interfaces to be passed through. In other words the transducer is advantageously placed as close as possible to the zone of treatment.

Such closeness also has the advantage of improving the accuracy with which the therapy is applied.

This approach has already been described in Document WO-A-89/07909, FIG. 5, where a rectal probe has been developed for treating tumors of the prostate. The device described is based on using two transducers incorporated in the rectal probe. One serves as a device for observing and locating the prostate, and the other serves to emit waves of ultrasound to perform the therapy.

The therapeutic transducer is coupled to a mirror for reflecting soundwaves. By coupling rotation of the mirror to displacement of the transducer relative to the mirror, it is possible to scan and treat a sector of the prostate. By rotating the assembly, it is possible to treat a given volume of the prostate. The transducer component and mirror must be capable of moving relative to one another over some distance in order to make it possible to treat the entire volume of the prostate. This gives rise to a mechanical device that is complex to the detriment of the ease with which it can be used and above all of its accuracy, as is required for this type of therapy.

In addition, that device cannot be used simultaneously to locate and to treat the tumor zone.

Each time a zone is located, it is necessary to displace the observation device to leave room for the treatment device.

A major drawback of this is loss in the accuracy with which treatment is applied, with such loss being due in part to tissue moving when the transducer components are moved. Another major drawback of that device is that progress of the treatment cannot be monitored in real time and the position of the probe cannot be corrected in real time as a function of the results obtained.

An object of the present invention is thus to solve the novel technical problem consisting in providing a solution for destroying tumor tissue (in particular of the prostate), the apparatus being simple to use, accurate, reliable, and capable of simultaneous monitoring in real time.

Another object of the invention is to solve the novel technical problem consisting in providing a solution for destroying tumor tissue (in particular of the prostate) by means of a solution that is sufficiently simple, accurate, and reliable for it to be possible to consider treating tumors (in particular of the prostate) at an early stage, i.e. when the lesions are small in size and thus require observation means and treatment means that are extremely accurate.

Another object of the present invention is to solve the novel technical problem specified above by approaching the tumor tissue via the rectum.

An object of the present invention is to solve the novel technical problem specified above by approaching the tumor tissue (in particular of the prostate) via the rectum, while simultaneously observing the tumor tissue in real time via endo-cavitary means.

Another object of the present invention is to solve the novel technical problems specified above by adopting a solution that makes it possible to approach the tumor tissue simultaneously via the rectum for the therapeutic device and via endo-cavitary means for the real time observation device.

Another object of the present invention is to solve the novel technical problems specified above by a solution that uses focused ultrasonic soundwaves of short duration and high intensity. In the description and the claims, the term "short duration" is used for periods of exposure to sound that are less than sixty seconds long, in contrast with conventional hyperthermia.

All of these technical problems are solved by the present invention simultaneously, simply, safely, and reliably in a manner that is susceptible of conventional manufacturing processes.

SUMMARY OF THE INVENTION

Thus, in a first aspect, the present invention provides a therapeutic endo-rectal probe comprising at least a piezo electric transducer element having a front face for emitting ultrasonic soundwaves and a rear face, wherein said transducer element is mounted in a support member itself connected to a rigid guide means enabling endo-rectal insertion of said probe, the outside shape of said support member preferably being that of a disk having an outline that is for the most part substantially circular or substantially elliptical, thereby facilitating endo-rectal insertion. As a result, it is advantageous for the outside shape of the transducer element itself to be disk-shaped with its profile being, for the most part, substantially circular or substantially elliptical. In a particular variant embodiment, the support member has an outside shape whose profile is substantially circular for the most part, but which has a smaller diameter in the direction perpendicular to the axis of the rigid guide compared with the diameter of the support member parallel to the axis of the rigid guide. Likewise, it is advantageous for the outside shape of the transducer element to be itself circular for the most part but with a smaller diameter in the direction perpendicular to the axis of the rigid guide compared with its diameter parallel to the axis of the rigid guide. The ratio of the diameter in the longitudinal axis direction divided by the transverse direction perpendicular thereto lies in the range 1 to 2, i.e. the shorter diameter may be as little as one-half the diameter in the direction parallel to the axis of the rigid guide. This shorter diameter may be obtained by any suitable method of manufacture. In particular, it may be obtained by cutting up or pairing down a part that has already been fabricated.

In accordance with another particularly advantageous feature of the invention, the outside periphery of the support member where it is largest is less than about 16 cm.

In a particularly advantageous embodiment, the above-mentioned support member is substantially closed, but includes a front face provided with an opening allowing the front face of the transducer element to be substantially uncovered so as to avoid interfering with the emission of ultrasonic waves.

In a particular embodiment, the above-mentioned support member is made in two portions, a front portion including the opening, and a rear portion which is removable from the front portion to provide easy access to the transducer.

In another particular embodiment, the above-mentioned guide comprises a rigid tube having a distal end on which the support member for the transducer element is mounted, and a proximal end enabling at least one electric wire to pass for powering the transducer element.

In yet another particular embodiment of the invention, the above-mentioned endo-rectal probe is characterized in that it includes a membrane that completely encloses in sealed manner said above-mentioned piezoelectric transducer element mounted on the support member, or the above-mentioned guide means, together with means for feeding the inside of the membrane with a liquid coupling medium, which feed means preferably comprise a feed pipe disposed inside the rigid guide means, with the free end of the pipe being inserted in a corresponding orifice in the support member, thereby providing communication with the space defined between the membrane and the support member.

In a particular variant embodiment, the above-mentioned membrane is constituted by a material that is thin and flexible, and that is transparent to soundwaves, e.g. a latex or a silicone.

In an advantageous variant embodiment, the above-mentioned membrane includes radial deformation means enhancing radial deformation of the membrane substantially without longitudinal deformation, thereby enabling the membrane to come into contact with the rectal wall without significantly distending along the longitudinal axis passing via the axis of the guide means.

Advantageously, the above-mentioned radial deformation means comprise a zone of reduced thickness of the membrane overlying the above-mentioned transducer element.

In another particular variant embodiment, the longitudinal size of the above-mentioned membrane parallel to the axis of the above-mentioned guide rod is greater than the longitudinal size of the support member, thereby enabling the support member to move in translation relative to the membrane and inside said membrane. When the membrane is deformed radially by the above-mentioned radial deformation means, the membrane can no longer be displaced and this feature of the invention makes it possible to obtain displacement motion of the transducer element support member, and thus of the transducer element, relative to the membrane, thus making it possible to treat the entire volume of the tumor tissue.

In another particular variant embodiment, the above-mentioned membrane is in the form of a bag into which the above-mentioned support member is inserted, with the opening of the bag being fixed in sealed manner to the support member or to the guide means.

The above-mentioned transducer element is preferably selected from the group constituted by conventional piezoelectrical ceramics and composite piezoelectrical ceramics.

The transducer element may be plane in shape and monolithic in design, being coupled to a focusing lens that is of monolithic design and in the form of a spherical cap, thereby naturally focusing the emitted soundwaves on the geometrical center of the sphere.

The transducer element may be a mozaic design with focusing being obtained by electronic means associated with each of the elements, or it may be of mozaic design and in the form of a spherical cap, with focusing then being obtained naturally.

In a preferred embodiment, constituting a feature that is independently patentable, the above-mentioned transducer element has a ratio of the diameter (d) of its ultrasonic wave emitting front face divided by its focal length (F) that is natural or obtained by electronic means, lying in the range about 0.5 to about 1.5, and preferably in the range 0.8 to 1.2, and better still about 1.

Advantageously, as mentioned above, the diameter of the transducer element in a direction perpendicular to the longitudinal axis of the probe is shorter than the diameter of the transducer element in the longitudinal direction of the probe, thereby facilitating insertion of the probe into the rectum, with the transducer element having a ratio of aperture diameter (d) relative to focal length (F) that is not constant. This may be achieved by the construction of the support member, or else by cutting off the sides of the piezoelectric element after it has been manufactured. A similar procedure is applied to the support member so that its outside shape and thus the amount of space it occupies is as close as possible to that of the piezoelectric transducer element, as can easily be understood on referring to the detailed description given below of several presently preferred embodiments of the invention described with reference to the accompanying figures.

In an advantageous embodiment, the focal length (F) of the transducer lies in the range 2 cm to 7 cm, and is ideally about 5 cm, depending on the desired penetration depth for the soundwaves. The diameter (d) lies in the range 2 cm to 7 cm, and is ideally about 5 cm, depending on the level of energy density that is acceptable or desirable at the transducer.

According to another advantageous feature of the invention, clearance exists between the transducer element and the support member thus advantageously making it possible to receive a backing layer having the purpose of improving the performance of the transducer element.

According to another advantageous feature of the invention, the front face of the above-mentioned piezoelectric transducer element is designed to be immersed in a soundwave coupling liquid. Sealing means are preferably provided to provide sealing between the front face and the rear face of the piezoelectric transducer element. Advantageously, the sealing means comprises an electrically conductive resin. It may also include an annular electrically insulating gasket providing electrical insulation for the rear face of the transducer element.

According to another embodiment of the invention, the endo-rectal probe further includes an imaging transducer.

According to a specific variant of this embodiment, the imaging transducer is secured to the therapy transducer and is thus in a position that is fixed relative thereto, the imaging transducer is separate and independent from the therapy transducer and points so that the image plane it forms continuously includes the axis of symmetry of the therapy transducer and includes the focal point, thereby making it possible to display the focal point and the treatment zone on a permanent basis.

According to another specific embodiment, the imaging transducer is located, in fixed position, under the therapy transducer, said therapy transducer comprising an acoustical window, from which said imaging transducer performs a sector scanning permanently covering the focal point and the treatment zone.

According to a particular feature, the imaging transducer performs a sector scanning.

According to another specific feature, the imaging transducer is a commercially available imaging probe which is secured to the support of the therapy transducer component by a fixing clamp. Preferably the fixing clamp includes guide means and optionally includes positioning means and sealing means.

According another specific variant, the imaging transducer operates at a frequency lying in a range from 3 MHz to 7 MHz.

In a second aspect, the present invention also provides apparatus for destroying tumor tissue, in particular of the prostate, characterized in that it comprises a therapeutic endo-rectal probe as defined above.

Also, and in manner that is independently patentable, the invention also relates to apparatus for destroying tumor tissue, in particular of the prostate, characterized in that it comprises a therapeutic endo-rectal probe combined with an imaging endo-cavitary probe, with the therapeutic endo-rectal probe being preferably as described above.

Advantageously, the imaging endo-cavitary probe is of the ultrasonic type, suitable for performing echography, with image-forming means being present.

In an advantageous embodiment, the endo-cavitary probe comprises a transducer element itself mounted on a support element of the endo-cavitary probe which is in turn mounted on a rigid guide means of the endo-cavitary probe.

According to a specific variant, the endo-cavitary probe is an endo-urethral probe.

In another advantageous embodiment that is independently patentable, the above-mentioned endo-rectal probe and the endo-urethral probe are mounted via their respective guide means on a common probe support device preferably comprising a rigid column mounted on a device for supporting the patient.

In another preferred embodiment, the above-mentioned endo-rectal probe and endo-urethral probe are mounted on the common support device for the above-mentioned probes via couplings including translation means enabling the probes to move in translation along an X-axis corresponding to the longitudinal axis of the patient and preferably including means for rotating the probes about the same X-axis.

In an advantageous variant embodiment, the common support device for the above-mentioned probes include means for putting the above-mentioned link elements simultaneously into translation motion while enabling the probes to be rotated independently.

In another advantageous variant embodiment, the above-mentioned couplings are slidably mounted along a Z-axis, perpendicular to the X axis, and advantageously substantially vertical, and with control means being provided to enable the couplings to move independently along the Z-axis.

In another advantageous embodiment of the apparatus of the invention, the apparatus is characterized in that it includes motor and stepdown gear box devices integrated in the couplings and controlled by a control device to displace the above-mentioned endo-rectal and endo-urethral probes in translation and/or in rotation.

Advantageously, the apparatus includes encoder devices integrated in the couplings for accurately measuring the displacement in translation and/or rotation of each of the above-mentioned endo-rectal and endo-urethral probes, together with means for transmitting said information concerning displacement in translation and/rotation to the control device.

In another advantageous embodiment, the control device comprises a central computer, in particular including control software which preferably comprises operator interface software together with software for managing commands via a command interface.

In another, particularly advantageous embodiment of the invention, the therapeutic endorectal probe further includes said imaging endo-cavitary probe comprising an imaging transducer, thereby having said imaging endo-cavitary probe physically linked to the therapeutic endo-rectal probe.

In a preferred variant embodiment, the imaging transducer is secured to the therapy transducer and is thus in a position that is fixed relative thereto, the imaging transducer is separate and independent from the therapy transducer and points so that the image plane it forms continuously includes the axis of symmetry of the therapy transducer and includes the focal point, thereby making it possible to display the focal point and the treatment zone on a permanent basis.

According to another specific embodiment, the imaging transducer is located, in fixed position, under the therapy transducer, said therapy transducer comprising an acoustical window through which said imaging transducer performs a sector scanning permanently covering the focal point and the treatment zone.

In a particular variant embodiment, the frequency of the imaging transducer lies in the range 3 MHz to 7 MHz.

In another variant embodiment, the imaging probe performs sector scanning.

In yet another variant embodiment, a commercially available imaging probe is used which is secured to the support for the therapy transducer element by means of a fixing clamp.

In another particular embodiment, the fixing clamp includes guide means and optionally positioning means together with sealing means.

All of the above-mentioned conclusive technical advantages are thus obtained in a manner that is simple, reliable, that provides better accuracy in application of the therapy, and that enables the overall duration of tumor tissue destruction therapy to be reduced, in particular when treating tumor tissue in the prostate.

BRIEF DESCRIPTION OF THE DRAWINGS

Embodiments of the invention are described by way of example with reference to the accompanying drawings, in which:

FIG. 2 is an axial view in longitudinal section on line II—II of FIG. 3 through the endo-rectal probe together with the rigid guide means supporting it;

FIG. 3 is a view looking along arrow III of FIG. 2;

FIG. 4 is a section view on line IV—IV of FIG. 3 through a first embodiment of a transducer element as shown in FIGS. 2 and 3;

FIG. 7 is a plan view of a third embodiment of a transducer element which is elliptical in shape;

FIG. 8 is a section view through the elliptical transducer element of FIG. 7 on line VIII—VIII of FIG. 7;

FIG. 9 shows a variant embodiment of the endo-rectal probe shown in FIGS. 1 to 4, including an axially-deformable inflatable membrane shown in the inflated state;

FIG. 10 is a block diagram of control members for the apparatus.

DETAILED DESCRIPTION

Figure 1:
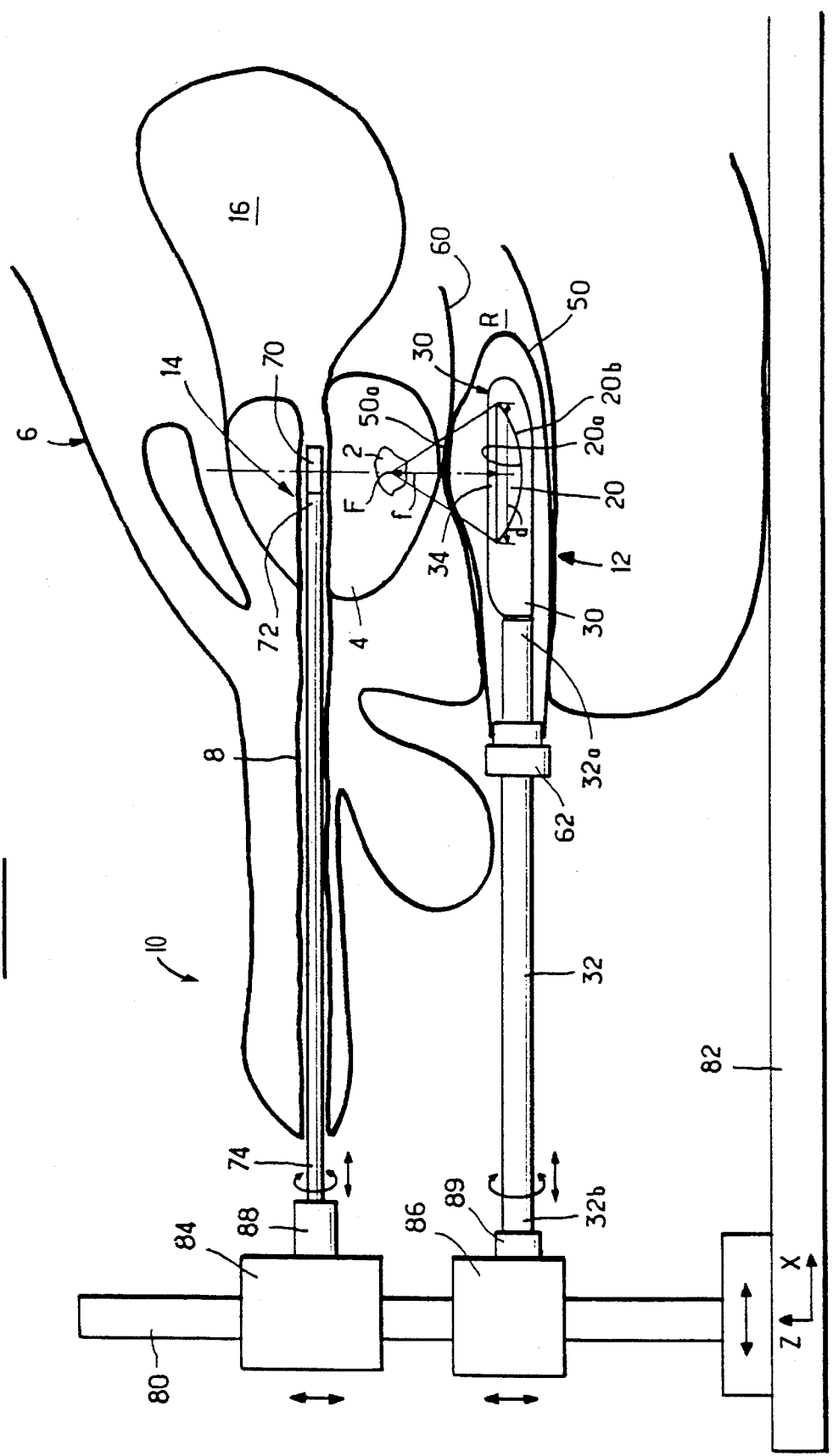
FIG. 1 is a diagrammatic profile view in partial section showing the therapeutic endo-rectal probe in position in the rectum together with an endo-cavitary probe here under the form of an endo-urethral probe in position in the urethra and level with the prostate.

With reference to the figures, and in particular to FIGS. 1 to 3, there can be seen apparatus for destroying tumor tissue 2, in particular of the prostate 4, with the apparatus being given overall reference numeral 10. The bladder is referenced 16, the patient is referenced 6, and the urethra 8. The apparatus comprises an endo-rectal probe 12 inserted in the rectum R, together with an endo-urethral probe 14 for observation purposes and inserted in the urethra 8.

In a presently preferred embodiment, the therapeutic endo-rectal probe 12 comprises at least one piezoelectric transducer element 20 having a front face 20a for emitting ultrasonic soundwaves and a rear face 20b. The transducer element 20 is mounted in a support member 30 which is itself connected to rigid guide means 32 enabling endo-rectal insertion of the probe to be performed, as can clearly be seen from the figures. The outside shape of the support member 30 is preferably in the form of a disk having an outline that is substantially circular (see FIG. 3) or that is substantially circular over a major portion (see FIG. 5), or that is substantially elliptical (see FIG. 7), thereby facilitating endo-rectal insertion.

In a particular variant embodiment, the support member 30 is substantially closed, but includes a front face 30a provided with an opening 34 which can be seen more clearly in FIG. 2, leaving the front face 20a of the transducer element 20 substantially completely uncovered, so as to avoid interfering with the emission of ultrasonic waves. The outside perimeter of the support member 30 is advantageously defined in such a manner that in a radial plane perpendicular to the longest longitudinal axis, it is never greater than about 16 cm. Advantageously, the support member 30 is made up of two portions: a front portion 35; and a rear portion 36, which portions can be taken apart to provide easy access to the transducer element 20. It may be observed that the front portion 35 is provided in this case with at least two radially projecting annular shoulders given respective references 37 and 38 for constituting reception surfaces respectively for the periphery of the transducer element 20 and for the rear portion 36.

It is advantageous to leave clearance between the transducer element 20 and the rear portion 36 of the support member 30 in order to leave room to receive an intermediate or backing layer having the function of improving the performance of the transducer element 20. The nature of such intermediate layers or backing is well known to the person skilled in the art.

The rear portion 36 is disconnectably fixed to the front portion 35 in any suitable manner, e.g. by means of fixing screws (not shown) but symbolized by axes 39. Sealing means 40 may be provided between the front and rear faces 20a and 20b of the transducer element. The sealing means 40 advantageously comprise a resin that is preferably electrically conductive. In addition, an electrically insulating gasket 42 may be provided (an annular gasket in this case) to insulate the rear face 20b of the transducer element 20 electrically.

The above-mentioned support guide 32 advantageously comprises a rigid tube that is seen more clearly in FIG. 2, having a distal end 32a on which the support element 30 for the transducer element is mounted and a proximal end 32b enabling at least one electrical wire 44 to pass along the tube to power the transducer element 20. It is preferable for the support member and the rigid guide 32 to be made of an electrically conductive material such as a metal, and in particular brass, and for it to be grounded as shown symbolically in FIG. 2. As a result, the electrical feed wire 44 serves merely to apply positive current to the transducer element 20 in a manner well known to the person skilled in the art.

In an advantageous embodiment of the invention, the endo-rectal probe 12 includes a membrane 50 which can clearly be seen in FIGS. 2 and 9, which membrane completely surrounds the piezoelectric transducer element 20, being mounted on the support member 30 or on the guide means 32. In the example shown it is mounted on the guide means 32 by means of a sleeve 62 enabling the guide 32 to move in rotation and in translation in a fully sealed manner, with means being provided to feed a liquid coupling medium 52 to the inside of the membrane 50. These feed means preferably comprise a feed pipe 54 disposed inside the hollow rigid tube 32, with the pipe engaging in a corresponding orifice formed through the solid support member 30, thereby putting the feed pipe 54 into communication with the space defined between the membrane 50, the sleeve 62, and the support member 30. The membrane 50 is advantageously constituted by a material that is thin and flexible, and that is transparent to soundwaves, e.g. a latex or a silicone. The sleeve 62 includes an annular groove 64 receiving the end or mouth 51 of the membrane 50 which is formed in this case into a pocket or bag, and also receiving means 66 such as a clamping collar for fixing the membrane 50 in place.

In another advantageous embodiment of the invention, the above-mentioned membrane 50 includes radial deformation means 56 for enhancing radial deformation of the membrane significantly without deforming it longitudinally, thereby enabling the membrane 50 to come into contact (at 50a) with a patient's rectal wall 60 without expanding significantly along the longitudinal axis defined by the axis of the guide means, and also referred to as the X-axis in FIG. 1.

The above-mentioned radial deformation means 56 preferably comprise a zone 50a of reduced thickness in the membrane overlying the above-mentioned transducer element, thereby ensuring contact with the rectum wall 60 over the entire area of the transducer element 20 and even over a greater longitudinal distance so that when the coupling liquid 52 is injected by suitable coupling of the injection means (not shown), good contact is provided with the rectal wall 60. The longitudinal size of the membrane 50 is preferably longer than that of the support member 30 so as to enable the support member 30 to move relative to the membrane 50, in particular in longitudinal translation, with the support member 30 moving inside the membrane 50 as will readily be understood on observing FIG. 9.

Advantageously, the transducer element 20 focuses the ultrasonic waves on a focal point and is preferably selected from the group constituted by conventional piezoelectric ceramics and by composite piezoelectric ceramics.

The transducer element may be of monolithic design, being plane in shape and coupled to a focusing lens that is of monolithic design and in the form of a spherical cap that naturally focuses soundwaves emitted at the geometrical center of the sphere.

Alternatively, the transducer element 20 may be of a mozaic design with focusing being obtained by electronic means associated with each of the elements in the mozaic, or the mozaic may be in the form of a spherical cap, with focusing being obtained naturally. In FIGS. 1 to 9, it will be seen that all of the embodiments show a presently preferred form where the transducer element is in the form of a spherical cap of the type having natural focusing.

In a preferred embodiment of the invention, the above-mentioned transducer element has a ratio of the diameter (d) of its ultrasound wave emitting front face 20a divided by its focal length (F) which may be natural or obtained by electronic means, that lies in the range above 0.5 to about 1.5, that lies preferably in the range about 0.8 to about 1.2, and better still is about 1.

With reference to FIGS. 1 to 4, a monolithic transducer element is shown that is in the form of a spherical cap of circular section having its diameter symbolized by d, its focus F, its focal length by f, and its bulk or apparent thickness e.

Figure 5:
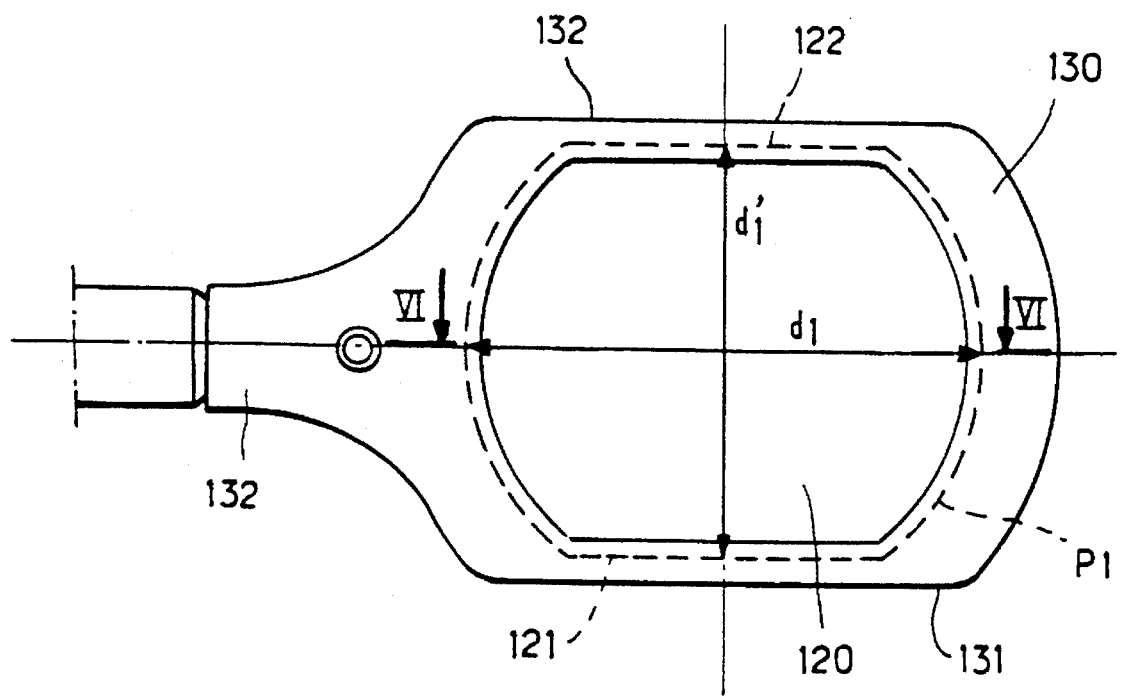
FIG. 5 is a plan view similar to FIG. 3 showing a second embodiment of an endo-rectal probe of the present invention having a smaller diameter in the direction perpendicular to the direction of longitudinal endo-rectal insertion.
Figure 6:
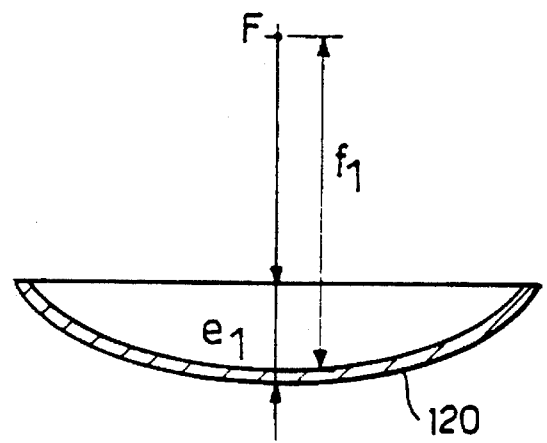
FIG. 6 is a section on line VI—VI of FIG. 5.

With reference to FIGS. 5 and 6, another embodiment of an endo-rectal probe is shown in which parts that perform the same function have been given the same reference numerals plus 100. It may be observed that the major portion of the outside shape of the transducer element 120 is substantially circular, with the same applying to the support member 130, but that the dimension (d'1) in a direction perpendicular to the axis of the rigid guide 132 is smaller than the diameter (d1) parallel to the axis of the rigid guide 132, as is clearly visible in FIG. 5. This smaller diameter d'1 may be obtained by cutting off the sides 121 and 122 of the transducer element 120, and similarly by cutting off the sides 131 and 132 of the support member 130, with the resulting shape facilitating endo-rectal insertion. As a result, the diameter of the transducer element 120 and also of the support member 130 varies instead of being constant. Advantageously, the ratio of the diameter in the longitudinal direction (d1) divided by the diameter in the direction perpendicular to the longitudinal axis (d'1) lies in the range 1 to 2. In accordance with another advantageous characteristic of the invention which is applicable to all embodiments, the outside perimeter P, P1 or P2 of the support member 30, 130 in the radial plane perpendicular to the longer longitudinal axis always remains below about 16 cm, thereby making endo-rectal insertion possible.

FIGS. 7 and 8 show another embodiment of a transducer element, with the reference numerals being increased by a further 100. Thus, the transducer element is referenced 220.

In this case, it is essentially elliptical in shape having a long diameter d2 extending parallel to the longitudinal axis of the patient 6, in this case the X-axis of FIG. 1. The shorter diameter is d'2 and its perimeter is P2, with its apparent thickness being e2, and its focal length being f2.

The focal length f, or f1 or f2 of the transducer element advantageously lies in the range 2 cm to 7 cm, and is ideally about 5 cm, depending on the penetration depth desired for the soundwaves. The diameter d or d' has a value lying in the range 2 cm to 7 cm, and is ideally about 5 cm, depending on the energy density level that is acceptable at the transducer element 20.

The particular geometrical shapes shown in FIGS. 5 to 8 have the advantage of increasing the emission area of the transducer without increasing its diameter, or of retaining the same emission area while reducing the area of the transducer.

In addition, the above-mentioned rigid guide 32 may be 20 cm long and may have a diameter of about 12 mm. In addition to having the function of containing the coupling liquid 52, the membrane 50 also provides a sterile barrier at the end of the rectal-probe 12. The membrane is itself sterile and is designed to be easily interchangeable, e.g. for use on a single occasion only.

According to an important characteristic of the invention, the above-mentioned apparatus includes an imaging endo-cavitary probe 14 shown in FIG. 1 in the form of an endo-urethral probe working in combination with the above-described endo-rectal probe. Note that in FIGS. 11 to 16, the imaging endo-cavitary probe is shown in the form of an imaging endo-rectal probe, comprising a commercially available endo-rectal imaging transducer.

Advantageously, the imaging endo-cavitary probe is of the ultrasonic type having image-forming means (not shown) for forming an image by echography.

According to another particular characteristic of the invention, the endo-cavitary transducer element 14 includes a transducer element 70 as can clearly be seen in FIG. 1, which probe is mounted on a support element 72 which is itself mounted on rigid guide means 74 for the endo-cavitary probe.

In reference to FIG. 1, the endo-rectal probe 12 and the endo-urethral probe 14 are preferably mounted via their respective guide means 32 and 74 on a common support device 80 for both probes 12 and 14, the support device preferably including a rigid column 80 mounted on a device 82 for supporting the patient.

According to a particular characteristic, the endo-rectal probe 12 and the endo-urethral probe 14 are mounted on the common support device 80 via couplings 84 and 86 including translation means 88 and 89 for moving the probes along an X-axis corresponding to the longitudinal axis of the patient. These couplings 84 and 86 preferably include means for rotating the probes about the same X-axis (e.g. integrated in the translation means 88 and 89).

According to a preferred characteristic, the common support device 80 includes the means 88 and 89 for moving the probes simultaneously in translation while enabling the probes to be rotated independently. Such means are well known to the person skilled in the art.

In an advantageous variant embodiment, the couplings 84 and 86 are slidably mounted along a Z-axis by being slidably mounted on the rigid column 80, with means being provided to control independent displacement of the couplings 84 and 86 along the Z-axis. Such control means are well known to the person skilled in the art and may comprise, for example, a rack and pinion system.

According to the invention, motor and stepdown gear box devices are integrated in the couplings 84 and 86 (given respective references 94 and 96 in FIG. 10) and they are controlled by a control device 90 (see FIG. 10) for displacing the endo-rectal and the endo-urethral probes in translation and/or in rotation.

Encoding devices 98 and 100 are also shown integrated in the couplings 84 and 86 (not shown explicitly in FIG. 10, but known to the person skilled in the art) and these encoding devices cooperate with the motor and gear box devices 94 and 96 to measure accurately the displacement in translation and/or in rotation of each of the probes 12 and 14 as represented diagrammatically in FIG. 10. Means 92 are also provided for transmitting this information concerning displacement in translation and/or rotation to the control device 90.

The control device 90 may include a central computer, in particular a computer containing control software, which software is preferably constituted by operator interface software and command management software. The control interface is advantageously a portion of the transmission means 92 shown in FIG. 10. Via the interfaces 92, the command management software controls the motors 94 and 96 integrated in the couplings 84 and 86 for moving the endo-rectal and endo-urethral probes and receives information concerning the displacement of the probes as transmitted by the encoders 98 and 100 integrated in the couplings 84 and 86.

The observation transducer element of the endo-urethral probe 14 is preferably of the ultrasonic type and thus constitutes an echograph. It provides an image plane of the urethral wall 8, of the prostate 4, and of the rectal wall 60 as can clearly be seen in FIG. 1. The support guide element 74 ensures that the transducer element 70 is rigidly positioned inside the urethra 8.

The endo-rectal and endo-urethral probes can be moved in translation and in rotation either manually or else using the above-mentioned motor devices 92 and 94 integrated in the couplings 84 and 86 and under the control of the control device 90. With reference to the figures, the apparatus operates as follows:

Initially the endo-urethral probe 14 is inserted into the urethra and is placed level with the prostate, in the position shown in FIG. 1.

The endo-rectal probe 12 is then inserted into the rectum and is placed facing the prostate as shown in FIG. 1.

The membrane 50 is then filled with coupling liquid which is injected via the inside of the guide tube 32 so that the thin zone 50a of the membrane deforms radially and comes into contact with the rectal wall 60.

The two probes 12 and 14 are then fixed relative to the common support 80 via the couplings 84 and 86. The positions of the couplings 84 and 86 are adjusted so as to cause the relative position of the two probes 12 and 14 so as to make the image plane of the endo-urethral probe 14 correspond with the midplane of the endo-rectal probe 12, thereby making it possible to keep the focus of the soundwaves from the probe 12 under permanent observation, as can clearly be seen in FIG. 1.

Thereafter, by displacing the probes 12 and 14 simultaneously in translation along the X-axis direction by means of the couplings 84 and 86, it is possible to retain this relative position and monitor the therapeutic process in real time.

Once they are properly positioned relative to each other, the relative position of the two probes is "frozen", thereby ensuring that real time monitoring can be continued throughout the therapeutic process.

The observation endo-urethral probe 14 provides a radial image plane through the prostate, thus making it possible to determine the Z and Y coordinates of the volume of tumor to be destroyed.

By displacing the endo-rectal and endo-urethral probes 12 and 14 simultaneously along the X-axis, it is possible to keep the prostate under permanent observation along the X-axis, thereby determining the X coordinates of the tumor volume to be destroyed.

The X, Y, and Z coordinates of the tumor volume to be destroyed are then recorded by the central computer 90.

Thereafter, the central computer 90 controls the motors 94 and 96 for displacing the probes 12 and 14 so as to scan and treat the entire tumor volume. By moving the therapeutic probe 12 along the Z-axis and by rotating it about the X-axis, it is possible to treat the prostate in a radial plane corresponding to the image plane of the probe 14. By displacing both probes 12 and 14 simultaneously along the X-axis it is also possible to treat successive planes, thereby treating the entire volume of the tumor to be destroyed while retaining the ability to monitor the therapeutic process in real time.

It will thus be understood that the invention also extends to a method of destroying tumor volumes, in particular in the prostate, the method comprising:

providing an endo-rectal therapeutic probe capable of emitting focused ultrasonic soundwaves;

providing an imaging endo-cavitary probe;

providing control means for controlling displacement of said probes in translation along an axis parallel to the longitudinal axis of the patient, and control means for controlling rotation of said probes about said axis, referred to as the "X-axis";

inserting the endo-rectal probe into the rectum to bring it level with the tumor volumes to be treated, in particular the prostate;

inserting the imaging endo-cavitary probe in regard to said tumor volumes to be treated, so that the image plane of the endo-cavitary probe corresponds to the midplane of the endo-rectal probe, thereby observing the focus of the soundwaves emitted from the endo-rectal probe; and when so desired, displacing in translation simultaneously the endo-rectal probe and the endo-cavitary probe, thereby treating the entire volume of the tumor to be destroyed while permanently observing the focus of the endo-rectal probe.

According to a particular embodiment of said method, said method comprises:

providing an endo-rectal therapeutic probe capable of emitting focused ultrasonic soundwaves;

providing an imaging endo-urethral probe;

providing control means for controlling displacement of said probes in translation along an axis parallel to the longitudinal axis of the patient, and control means for controlling rotation of said probes about said axis, referred to as the "X-axis";

control means for controlling displacement of said probes in translation along an axis perpendicular to said X-axis, thereby enabling the said probes to be moved towards each other or away from each other along an axis referred to as the "Z-axis";

inserting the endo-urethral probe into the urethra to bring it level with the tumor volumes to be treated, in particular the prostate;

inserting the endo-rectal probe into the rectum to bring it level with the tumor volumes to be treated, in particular the prostate;

fixing both the endo-urethral probe and the endo-rectal probe to a common probe support device so that the image plane of the endo-urethral probe corresponds to the midplane of the endo-rectal probe, thereby observing the focus of the soundwaves emitted from the endo-rectal probe; and simultaneously displacing both the endo-urethral probe and the endo-rectal probe along the X-axis during the therapeutic process so as to cover the volume of the tumor to be destroyed.

When so desired, the endo-rectal probe is also displaced in translation along the Z-axis while rotating the endo-rectal probe about the X-axis, thereby treating the entire volume of the tumor to be destroyed.

According to another specific embodiment, the endo-cavitary probe is physically linked to the endo-rectal probe, thereby facilitating insertion of the two probes in a single step and also avoiding the step of putting in proper position the imaging endo-cavitary probe with regard to the endo-rectal probe.

In an advantageous variant implementation of the method of the invention, the endo-rectal probe includes a transducer element that is focused naturally or electronically, and in which the ratio of its diameter to its focal length lies in the range 0.5 to 1.5, and preferably in the range 0.8 to 1.5, and better still is about 1.

In another advantageous implementation of the invention, the transducer element 20 is caused to emit ultrasound waves pulsed at a frequency lying in the range 1 MHz to 4 MHz with pulses that are of short duration, lying in the range 50 ms to 5 s, and preferably in the range 200 ms to 2 s, with the intensity at the focus lying in the range 1,000 W/cm$^2$ to 10,000 W/cm$^2$.

It should also be observed that the longitudinal length of the above-mentioned membrane is sufficient to enable the support member to move in axial translation, and in particular its radial deformation means extend longitudinally over a distance greater than the longitudinal length of the support member so as to enable displacement movement of the support member, in particular in translation, inside the membrane without losing contact between the membrane and the rectal wall.

Figure 11:
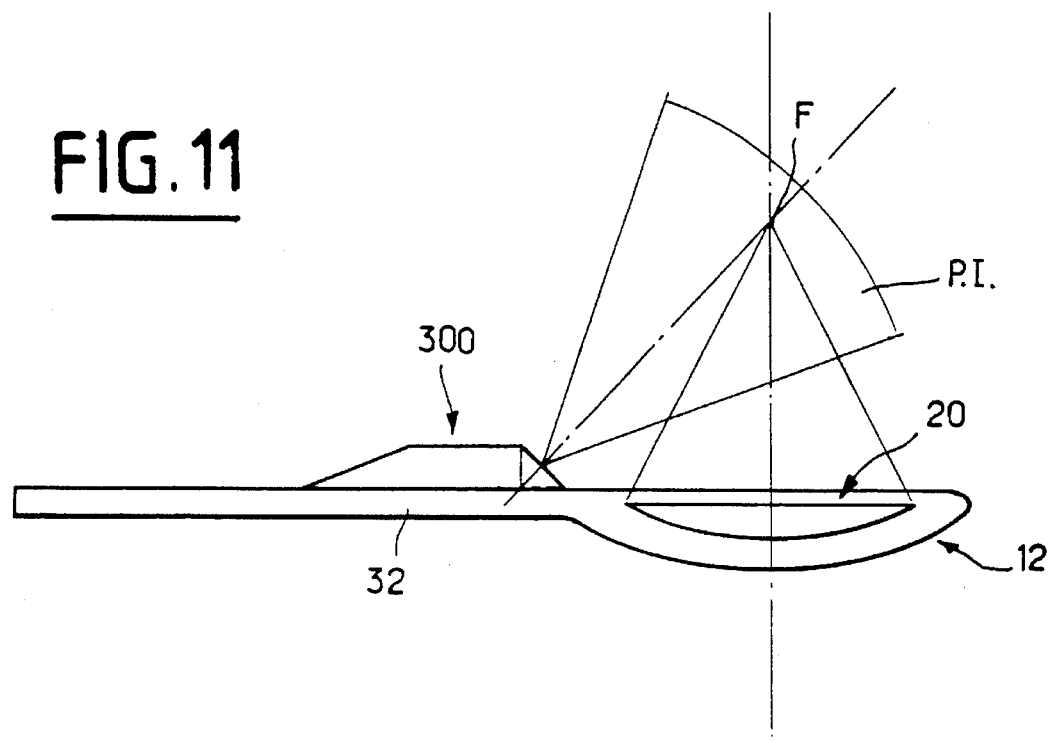
FIG. 11 shows another embodiment of a therapeutic endorectal probe of the present invention diagrammatically and in fragmentary section, this endorectal probe further including an imaging endo-cavitary probe comprising an imaging transducer, said imaging endo-cavitary probe constituting an imaging endo-rectal probe, with the present view being similar to that of FIGS. 4 and 9.
Figure 12:
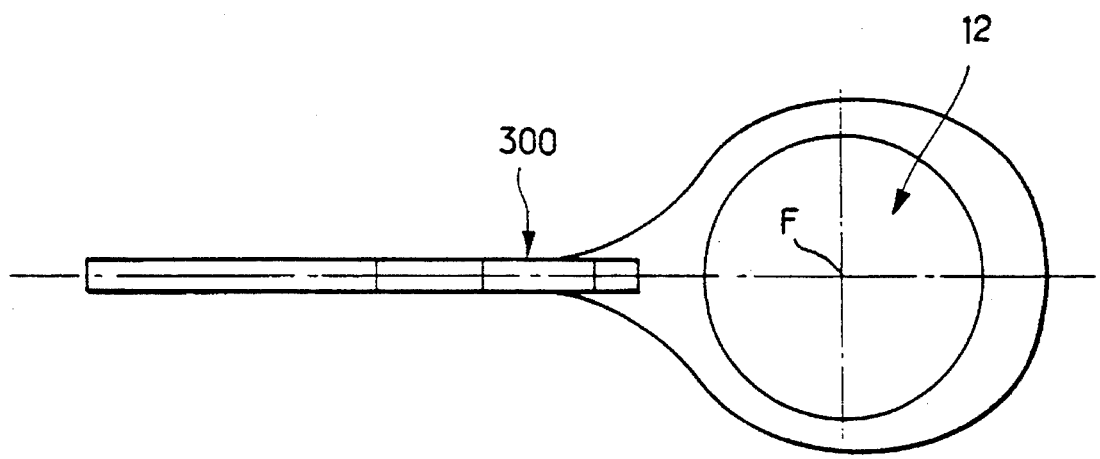
FIG. 12 is a plan view of the endorectal probe of FIG. 11.

In yet another advantageous embodiment of the invention as shown in FIGS. 11 and 12, the therapeutic endo-rectal probe 12 is of the same type as that described with reference to FIGS. 1 to 4 and further includes an imaging endo-cavitary probe comprising an imaging transducer designated by overall reference numeral 300. This imaging endo-cavitary probe is secured to the therapy transducer 20 via the endo-rectal probe 12, thereby constituting an imaging endo-rectal probe of a fixed position relative to the endo-rectal probe 12. The imaging transducer 300 is advantageously separate, being independent from the therapy transducer and pointing so that its image plane as symbolized by the letters PI continuously includes the axis of symmetry shown in FIG. 11 of the therapy transducer 20 and the focal point F, thereby enabling the focal point and the treatment zone to be continuously displayed.

In a particular variant embodiment, the imaging probe 300 performs by sector scanning, as shown.

In the example shown in FIGS. 11 and 12, the imaging transducer element 300 is secured to the support 32 of the endorectal probe 12, e.g. by gluing.

Figure 13:
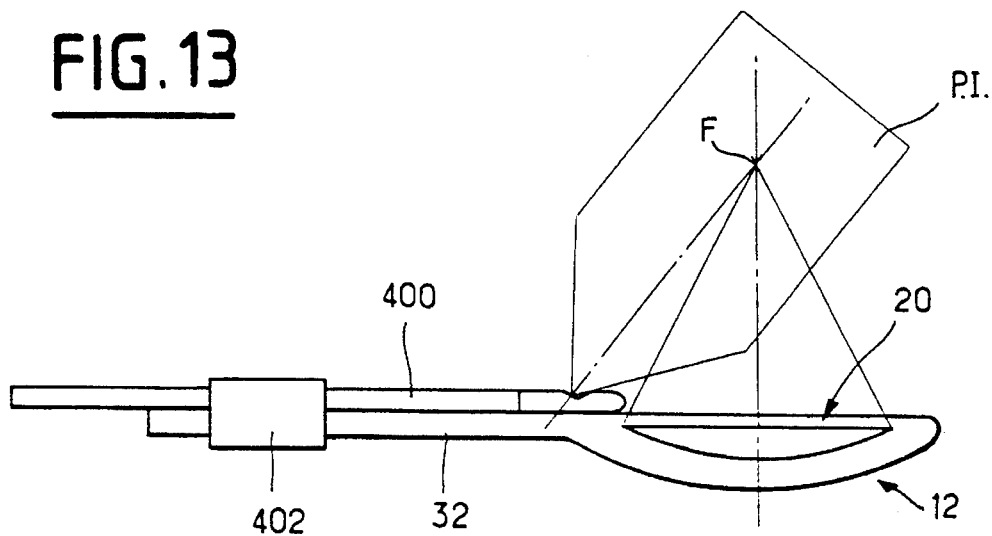
FIG. 13 shows another embodiment of an endorectal probe of the invention fitted with an imaging endo-cavitary probe here comprising a commercially available endo-rectal imaging transducer by means of a fixing clamp.
Figure 14:
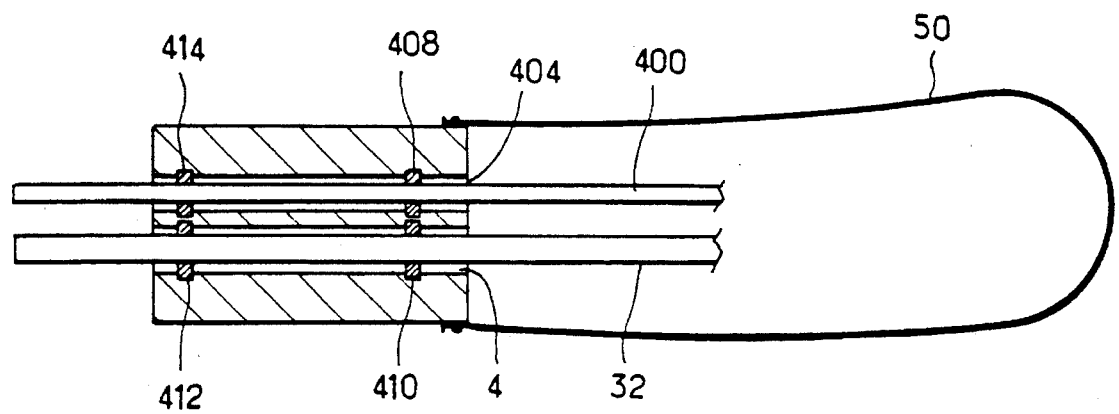
FIG. 14 is a longitudinal axial section view through the fixing clamp as seen on arrow XIV of FIG. 13.

In another embodiment shown in FIGS. 13 and 14, the endorectal probe 12 also includes an endo-cavitary probe 400 comprising a commercially available endo-rectal imaging transducer which is secured to the support 32 of the endorectal probe 12 and thus to the therapy transducer 20 by means of a fixing clamp 402 which is shown in greater detail in FIG. 14. The fixing clamp 402 advantageously includes guide means formed in this case by two longitudinal channels 404 and 406, and it extends over a sufficient length longitudinally in order to be able to perform this guidance function. In addition, sealing means such as O-rings are advantageously provided such as 408 & 410, and 412 & 414. These sealing means are advantageous insofar as it is possible to provide a membrane 50 filled with liquid and surrounding the therapy and imaging transducer elements 12 and 400 as in the preceding embodiments.

The advantage of this embodiment shown in FIGS. 13 and 14 lies in the fact that it is possible to use commercially available imaging probes which are merely inserted in the guide channel 404 until they take up the precise position shown in FIG. 13 which forms an integral part of the invention. In this position, the imaging transducer 400 is set back from the therapy transducer 20, thus ensuring that it does not interfere with it in any way while nevertheless having its image plane PI pointed to occupy the axis of symmetry of the therapy transducer 12 on a permanent basis, including the focal point F, thereby making it possible as in the preceding embodiment, to display the focal point and the treatment zone on a permanent basis.

Figure 15:
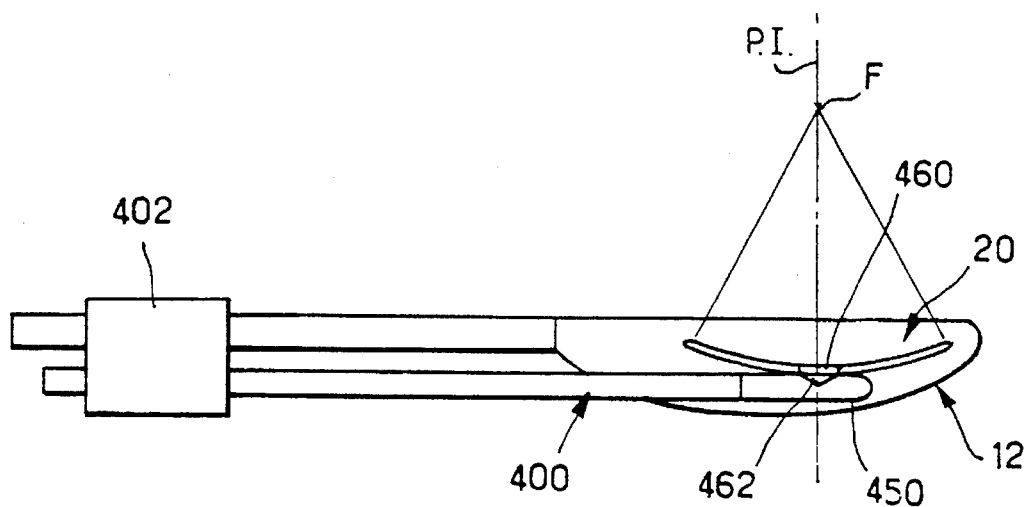
FIG. 15 shows a further embodiment of an endo-rectal probe of the invention of a structure allowing insertion of an imaging endo-cavitary probe, here comprising a commercially available endo-rectal imaging transducer, under the therapy transducer which comprises an acoustical window through which said imaging transducer performs a sector scanning permanently covering the focal point and the treatment zone.
Figure 16:
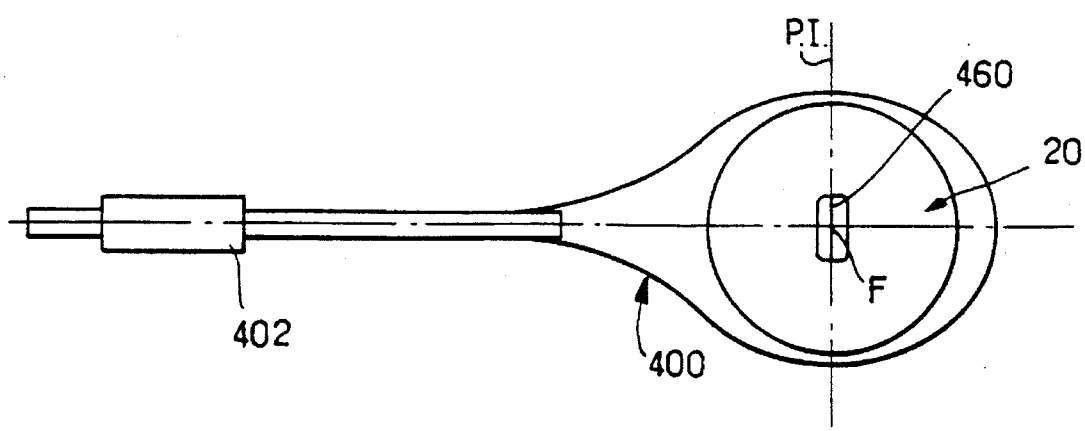
FIG. 16 is a plan top view of the endo-rectal probe of FIG. 15.

In a further embodiment shown in FIGS. 15 and 16, which represents a variant of the embodiments shown in FIGS. 13 and 14, the same reference numbers have been used for identical parts. Here it will be clearly understood for one skilled in the art that the imaging endo-cavitary probe 400 is inserted in a blind opening 450 which extends at least in part under the therapy transducer 20. The therapy transducer 20 comprises an acoustical window 460 under which is positioned the acoustic source 462 of the imaging probe 400 thereby allowing image scanning through the acoustic window 460 according to an image plane permanently covering the focal point and the treatment zone. Here it can be shown from FIG. 16 that the image plane is substantially perpendicular to the symmetry axis of the endo-rectal probe since it represents the scanning plane which is obtained with the commercially available endo-rectal probes.

In a preferred embodiment, the imaging transducer 300 or 400 operates at a frequency lying in the range 3 MHz to 7 MHz.

It should be observed that the description of FIGS. 1 to 16 and that FIGS. 1 to 16 themselves form integral parts of the invention and thus of the present description. The invention also covers any characteristic that appears to be novel over the prior art and that can be deduced from the above description including accompanying FIGS. 1 to 16.

We claim:

1. A probe for insertion in a body cavity, comprising: at least one piezoelectric transducer element for effecting therapeutic treatment and having a predetermined maximum cross-sectional perimeter, said piezoelectric transducer element having a front face defining a surface area for emitting ultrasound waves focused at a focus for effecting said therapeutic treatment, and a rear face;

a probe support member having a proximal end and a distal end and defining a longitudinal axis, said piezoelectric transducer element being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element; and a flexible membrane mounted to said probe support member and surrounding said distal end of said probe support member and said transducer element for providing a fluid seal thereabout, and means extending from the proximal end of said probe support member to said membrane for communicating fluid from said proximal end of said probe support member to said membrane for expanding same, whereby, the efficiency of said ultrasound waves for therapeutic treatment is maximized.

2. The probe according to claim 1, wherein said front face of said transducer element has a shape selected from the group consisting of substantially circular, substantially circular with truncated longitudinally extending side portions, and substantially elliptical.

3. The probe according to claim 2, wherein said probe support member has a front face defining an opening for receiving said transducer element, said front face of said transducer element confronting said front face of said support member when said transducer element is received in said opening.

4. The probe according to claim 3, wherein said maximum cross-sectional perimeter of said probe support member is less than about 16 cm.

5. The probe according to claim 4, further comprising a flexible membrane mounted to said probe support member and surrounding said distal end of said probe support member and said transducer element for providing a fluid seal thereabout, and means extending from the proximal end of said probe support member to said membrane for communicating fluid from said proximal end of said probe support member to said membrane for expanding same.

6. The probe according to claim 5, further comprising means for sealing said transducer element to said probe support member for preventing fluid at said front face of said transducer element from reaching said rear face thereof.

7. The probe according to claim 5, wherein the ratio of a diameter d of said front face of said transducer element to the focal length F of said transducer element is 0.5 to about 1.5.

8. The probe according to claim 7, wherein the shape of said front face of said transducer element is substantially circular with truncated longitudinally extending side portions, and wherein the ratio of the diameter of said front face of said transducer element in the longitudinal direction divided by the diameter in a direction perpendicular thereto is in the range of 1 to 2.

9. The probe according to claim 8, further comprising an imaging endo-cavitary probe for generating an image of said focus for monitoring said therapeutic treatment.

10. The probe according to claim 8, wherein said imaging endo-cavitary probe is secured to said probe support member.

11. The probe according to claim 1, wherein said probe support member has a front face defining an opening for receiving said transducer element, said front face of said transducer element confronting said front face of said probe support member when said transducer element is received in said opening.

12. The probe according to claim 11, wherein said front face of said transducer element is concave.

13. The probe according to claim 11, further comprising a backing layer disposed between said rear face of said transducer element and said probe support member for improving the performance of said transducer element.

14. The probe according to claim 1, wherein said maximum cross-sectional perimeter of said probe support member is about 16 cm.

15. The probe according to claim 1, further comprising electrical conducting means extending from the proximal end of said probe support member to the distal end thereof and connected at said distal end to the rear face of said transducer element.

16. The probe according to claim 1, further comprising means for sealing said transducer element to said probe support member for preventing fluid at said front face of said transducer element from reaching said rear face thereof.

17. The probe according to claim 1, wherein said membrane comprises radial deformation means for enhancing radial expansion of said membrane relative to longitudinal deformation.

18. The probe according to claim 1, wherein said membrane is mounted to said probe support member for longitudinal movement of said probe support member relative to said membrane.

19. The probe according to claim 1, wherein said piezoelectric transducer element is constructed from a material selected from the group consisting of piezoelectric ceramics and composite piezoelectric ceramics.

20. The probe according to claim 1, wherein said piezoelectric transducer element is selected from the group consisting of a monolithic design and a mosaic design comprising a plurality of transducer elements.

21. The probe according to claim 20, wherein said transducer element comprises a spherical cap for focusing the ultrasound waves generated thereby.

22. The probe according to claim 20, wherein said piezoelectric transducer element is a mosaic design comprising a plurality of transducer elements, and further comprising electronic means connected to said transducer elements for focusing at said focus the ultrasound waves emitted thereby.

23. The probe according to claim 1, wherein the ratio of a diameter d of said front face of said transducer element to the focal length F of said transducer element is 0.5 to about 1.5.

24. The probe according to claim 23, wherein said ratio is about 0.8 to about 1.2.

25. The probe according to claim 24, wherein said ratio is about 1.0.

26. The probe according to claim 1, further comprising an imaging endo-cavitary probe for generating an image of said focus for monitoring said therapeutic treatment.

27. The probe according to claim 26, wherein said imaging endo-cavitary probe is secured to said probe support member.

28. A probe for insertion in a body cavity, comprising:

at least one piezoelectric transducer element for effecting therapeutic treatment and having a predetermined maximum cross-sectional perimeter, said piezoelectric transducer element having a front face defining a surface area for emitting ultrasound waves focused at a focus for effecting said therapeutic treatment, and a rear face; and a probe support member having a proximal end and a distal end and defining a longitudinal axis, said piezoelectric transducer element being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element, the shape of said front face of said transducer element is substantially circular with truncated longitudinally extending side portions, and wherein the ratio of the diameter of said front face of said transducer element in the longitudinal direction divided by the diameter in a direction perpendicular thereto is in the range of 1 to 2.

29. A probe for insertion in a body cavity, comprising:

at least one piezoelectric transducer element for effecting therapeutic treatment and having a predetermined maximum cross-sectional perimeter, said piezoelectric transducer element having a front face defining a surface area for emitting ultrasound waves focused at a focus for effecting said therapeutic treatment, and a rear face;

a probe support member having a proximal end and a distal end and defining a longitudinal axis, said piezoelectric transducer element being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element; and, an imaging endo-cavitary probe for generating an image of said focus for monitoring said therapeutic treatment, the proximal end of said probe support member comprises a rigid guide member, and wherein said imaging endo-cavitary probe is secured to said rigid guide member for axial movement relative thereto.

30. A probe for insertion in a body cavity, comprising:

at least one piezoelectric transducer element for effecting therapeutic treatment and having a predetermined maximum cross-sectional perimeter, said piezoelectric transducer element having a front face defining a surface area for emitting ultrasound waves focused at a focus for effecting said therapeutic treatment, and a rear face;

a probe support member having a proximal end and a distal end and defining a longitudinal axis, said piezoelectric transducer element being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element; and an imaging endo-cavitary probe for generating an image of said focus for monitoring said therapeutic treatment, said piezoelectric transducer element having an acoustic window therein, and said imaging endo-cavitary probe being positioned beneath said acoustic window.

31. A method for treating a tumor volume, comprising:

providing an endo-rectal therapeutic probe having a longitudinal axis and incorporating emitting means for emitting ultrasound waves focused at a focus;

providing an imaging endo-cavitary probe having a longitudinal axis for imaging an image plane;

inserting the endo-rectal probe into the rectum until said emitting means confronts the tumor volume to be treated;

inserting the imaging endo-cavitary probe into a non-rectal cavity until the image plane of the endo-cavitary probe includes said focus for observing the focus of the ultrasound waves emitted by said endo-rectal probe; and simultaneously displacing in translation the endo-rectal probe and the endo-cavitary probe for treating the entire volume of the tumor while observing the focus of the endo-rectal probe.

32. The method according to claim 31, further comprising the step of rotating at least one of said probes about their respective longitudinal axes.

33. The method according to claim 31, further comprising the step of adjusting the relative positions of said endo-rectal and endo-cavitary probes for establishing said focus in said image plane whereby said focus remains in said image plane for imaging by said imaging endo-cavitary probe during said step of simultaneously displacing said probes in translation.

34. The method of claim 31, wherein said step of providing an imaging endo-cavitary probe comprises providing an imaging endo-urethral probe, and wherein said step of treating the entire volume of the tumor comprises treating the entire volume of a tumor in the prostate.

35. Apparatus for treating a tumor volume, comprising:

an endo-rectal therapeutic probe having a longitudinal axis and incorporating emitting means for emitting ultrasound waves focused at a focus, said endo-rectal probe being insertable into the rectum until said emitting means confronts the tumor volume to be treated;

an imaging endo-cavitary probe having a longitudinal axis for imaging an image plane, said imaging endo-cavitary probe being insertable into a non-rectal cavity until the image plane of the endo-cavitary probe includes said focus for observing the focus of the ultrasound waves emitted by said endo-rectal probe; and means for simultaneously displacing in translation the endo-rectal probe and the endo-cavitary probe for treating the entire volume of the tumor while observing the focus of the endo-rectal probe.

36. The apparatus according to claim 35, further comprising means for rotating at least one of said probes about their respective longitudinal axes.

37. The apparatus according to claim 35, further comprising means for adjusting the relative positions of said endo-rectal and endo-cavitary probes for establishing said focus in said image plane whereby said focus remains in said image plane for imaging by said imaging endo-cavitary probe during treatment of said tumor volume.

38. The apparatus according to claim 37, wherein said means for adjusting the relative positions of said endo-rectal and endo-cavitary probes comprises a common support and means for coupling said endo-rectal and endo-cavitary probes to said common support for independent movement relative thereto.

39. The apparatus according to claim 35, wherein said imaging endo-cavitary probe comprises an imaging endo-urethral probe.

40. A probe for insertion in a body cavity, comprising:

a probe support member having a proximal end and a distal end and defining a longitudinal axis;

at least one piezoelectric transducer element operative to emit ultrasound waves at a focus and effective for therapeutic treatment of body tissue and having a predetermined maximum cross-sectional perimeter, said piezoelectric transducer element being mounted on said probe support member at the distal end thereof, said piezoelectric transducer element being of a substantially disk shape, having a rear face and front face, said front face defining a surface area also of substantially disk shape and disposed substantially parallel to said longitudinal axis for emitting said ultrasound waves in a direction transversely to said longitudinal axis and focused at a focus for effecting said therapeutic treatment at said focus;

said distal end of said probe support member having a maximum cross-sectional perimeter conforming closely to said maximum cross-sectional perimeter of said piezoelectric transducer element of substantially disk shape for facilitating insertion of said probe in said body cavity and for maximizing the emitting surface area of said piezoelectric transducer element, whereby the efficiency of said transducer element in delivering said ultrasound waves at said focus is maximized;

a flexible membrane mounted to said probe support member and surrounding said distal end of said probe support member and said transducer element for providing a fluid seal thereabout; and means extending from the proximal end of said probe support member to said membrane for communicating fluid from said proximal end of said probe support member to said membrane for expanding said membrane.

41. The probe according to claim 40, further comprising means for sealing said transducer element to said probe support member for preventing fluid at said front face of said transducer element from reaching said rear face thereof.

42. The probe according to claim 40, wherein said membrane comprises radial deformation means for enhancing radial expansion of said membrane.

43. The probe according to claim 40, wherein said membrane is mounted to said probe support member for longitudinal movement of said probe support member relative to said membrane.

44. The probe according to claim 40, wherein said piezoelectric transducer element is constructed from material selected from the group consisting of piezoelectric ceramics and composite piezoelectric ceramics.

45. The probe according to claim 40, wherein said piezoelectric transducer element is a mosaic design comprising a plurality of transducer elements, and further comprising electronic means connected to said transducer elements for focusing at said focus the ultrasound waves emitted thereby.

46. The probe according to claim 40, wherein the ratio of a diameter d of said front face of said transducer element to the focal length F of said transducer element is 0.5 to about 1.5.

47. The probe according to claim 46, wherein said ratio is about 0.8 to about 1.2.

48. The probe according to claim 47, wherein said ratio is about 1.0.

49. A probe for insertion in a body cavity, comprising:

a probe support member having a proximal end and a distal end and defining a longitudinal axis;

at least one piezoelectric transducer element operative to emit ultrasound waves at a focus and effective for therapeutic treatment of body tissue and having a predetermined maximum cross-sectional perimeter, said piezoelectric transducer element being mounted on said probe support member at the distal end thereof, said piezoelectric transducer element being of substantially disk shape, having a rear face and a front face, said front face defining a surface area having substantially circular shape with truncated longitudinally extending side portions, said front face being dimensioned so that the ratio of the diameter of said front face of said transducer element in the longitudinal direction divided by the diameter in a direction perpendicular thereto is in the range of 1 to 2;

said front face being disposed substantially parallel to said longitudinal axis for emitting said ultrasound waves transversely to said longitudinal axis and focused at a focus for effecting said therapeutic treatment at said focus; and said distal end of said probe support member having a maximum cross-sectional perimeter conforming closely to said maximum cross-sectional perimeter of said piezoelectric transducer element of substantially disk shape for facilitating insertion of said probe in said body cavity and maximizing the emitting surface area of said piezoelectric transducer element, whereby the efficiency of said transducer element in delivering said ultrasound waves at said focus is maximized.

50. A probe for insertion in a body cavity, comprising:

a probe support member having a proximal end and a distal end and defining a longitudinal axis, said proximal end comprising a rigid guide member;

at least one piezoelectric transducer element operative to emit ultrasound waves at a focus and effective for therapeutic treatment of body tissue and having a predetermined maximum cross-sectional perimeter, said piezoelectric transducer element being mounted on said probe support member at the distal end thereof, said piezoelectric transducer element being of substantially disk shape, having a rear face and a front face;

said front face being disposed substantially parallel to said longitudinal axis for emitting said ultrasound waves transversely to said longitudinal axis and focused at a focus for effecting said therapeutic treatment at said focus;

an imaging endo-cavitary probe for generating an image of said focus for monitoring said therapeutic treatment, said endo-cavitary probe being secured to said rigid guide member for axial movement relative to said rigid guide member;

said distal end of said probe support member having a maximum cross-sectional perimeter conforming closely to said maximum cross-sectional perimeter of said piezoelectric transducer element of substantially disk shape for facilitating insertion of said probe in said body cavity and maximizing the emitting surface area of said piezoelectric transducer element, whereby the efficiency of said transducer element in delivering said ultrasound waves at said focus is maximized.

51. A probe for insertion in a body cavity, comprising:

a probe support member having a proximal end and a distal end and defining a longitudinal axis;

at least one piezoelectric transducer element having an acoustic window therein and operative to emit ultrasound waves at a focus and effective for therapeutic treatment of body tissue and having a predetermined maximum cross-sectional perimeter, said piezoelectric transducer element being mounted on said probe support member at the distal end thereof, said piezoelectric transducer element being of substantially disk shape, having a rear face and a front face;

said front face being disposed substantially parallel to said longitudinal axis for emitting said ultrasound waves transversely to said longitudinal axis and focused at a focus for effecting said therapeutic treatment at said focus;

an imaging endo-cavitary probe for generating an image of said focus for monitoring said therapeutic treatment, said endo-cavitary probe being positioned beneath said acoustic window;

said distal end of said probe support member having a maximum cross-sectional perimeter conforming closely to said maximum cross-sectional perimeter of said piezoelectric transducer element of substantially disk shape for facilitating insertion of said probe in said body cavity and maximizing the emitting surface area of said piezoelectric transducer element, whereby the efficiency of said transducer element in delivering said ultrasound waves at said focus is maximized.

52. A probe for insertion in a body cavity, comprising:

a probe support member having a proximal end and a distal end having a front face defining an opening therein, said support member defining a longitudinal axis;

at least one piezoelectric transducer element operative to emit ultrasound waves at a focus effective for therapeutic treatment of body tissue and having a predetermined maximum cross-sectional perimeter, said piezoelectric transducer element being of a substantially disk shape having a rear face and a front face, and being mounted in said opening with the front face of said transducer element confronting the front face of said support member;

said front face defining a surface area also of substantially disk shape which is disposed substantially parallel to said longitudinal axis for emitting said ultrasound waves transversely to said longitudinal axis and focused at a focus for effecting said therapeutic treatment at said focus;

said distal end of said probe support member having a maximum cross-sectional perimeter conforming closely to said maximum cross-sectional perimeter of said piezoelectric transducer element of substantially disk shape for facilitating insertion of said probe in said body cavity and maximizing the emitting surface area of said piezoelectric transducer element, whereby the efficiency of said transducer in delivering said ultrasound waves at said focus is maximized.

53. A method for treating a body zone located inside the body of a patient, comprising the steps of:

providing a probe for insertion in a body cavity near said body zone of said patient, said probe including at least one piezoelectric transducer element operative to emit ultrasound waves at a focus effective for therapeutic treatment of the body tissue and having a predetermined maximum cross-sectional perimeter, said piezoelectric transducer element having a front face defining a surface area for emitting ultrasound waves focused at a focus for effecting said therapeutic treatment, and a rear face, and further including a probe support member having a proximal end and a distal end and defining a longitudinal axis, said piezoelectric transducer element being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element;

providing a flexible membrane mounted to said probe support member and surrounding said distal end of said probe support member and said transducer element for providing a fluid seal thereabout and defining a chamber between said membrane and said probe support member;

inserting said probe into said body cavity near said body zone to be treated, with said front face of said piezoelectric transducer element in front of said body zone to be treated, said focus being located in said body zone;

providing means extending from the proximal end of said probe support member to said membrane for communicating fluid from said proximal end of said probe support member to said membrane for expanding same;

inflating said membrane after said probe is inserted into said body cavity near said body zone to be treated for moving said membrane into contact with the inside wall of the body cavity; and causing said piezoelectric transducer element to emit ultrasound waves effective for said therapeutic treatment at said focus in said body zone.

54. The method of claim 53, wherein said body zone is a tumor located inside the body of a patient.

55. The method of claim 53, wherein said body zone is a prostate tumor.

56. The method of claim 55, including:

providing said probe, comprising said at least one piezoelectric transducer element and said probe support member, as an endorectal therapeutic probe having a longitudinal axis;

inserting said endorectal probe into the rectum until said front face confronts the prostate tumor volume to be treated;

causing said piezoelectric transducer element to emit ultrasound waves effective for said therapeutic treatment at said focus; and displacing said endorectal probe for treating the entire volume of the tumor.

57. The method of claim 53, wherein said causing step includes causing said piezoelectric transducer element to emit ultrasound waves pulsed at a frequency in the range from 1 MHz to 4 MHz with pulses of short duration ranging between 50 milliseconds and 5 seconds.

58. The method of claim 53, including delivering an intensity at the focus in the range from 1,000 W/cm$^2$ to 10,000 W/cm$^2$.

59. The method of claim 57, wherein the pulses have a short duration ranging between 200 milliseconds and 2 seconds.

60. The method of claim 53, including selecting the shape of the front face of said transducer element from the group consisting of substantially circular, substantially circular with truncated longitudinally extending side portions, and substantially elliptical.

61. The method of claim 53, wherein said providing step comprises providing a probe having a probe support member including a front face defining an opening for receiving said transducer element, said rear face of said transducer element confronting said front face of said probe support member when said transducer element is received in said opening.

62. The method of claim 53, wherein said maximum cross-sectional perimeter of said probe support member is about 16 cm.

63. The method of claim 53, including providing said membrane with radial deformation means for enhancing radial expansion of said membrane relative to longitudinal deformation.

64. The method of claim 53, further providing a piezoelectric transducer element having the ratio of a diameter d of said front face of said transducer element to the focal length F of said transducer element ranging between about 0.5 and about 1.5.

65. The method of claim 64, wherein said ratio is ranging between about 0.8 and about 1.2.

66. The method claim 53, further comprising providing an imaging endocavitary probe for generating an image of said focus for monitoring said therapeutic treatment.

67. The method of claim 66, further comprising securing said imaging endocavitary probe to said probe support member.

68. A method for treating a body zone located inside the body of a patient, comprising the steps of:

providing a probe for insertion in a body cavity near said body zone of said patient, said probe including a probe support member having a proximal end and a distal end and defining a longitudinal axis;

at least one piezoelectric transducer element mounted on said probe support member at the distal end thereof, said piezoelectric transducer element being operative to emit ultrasound waves at a focus effective for therapeutic treatment of body tissue and having a predetermined maximum cross-sectional perimeter, said piezoelectric transducer element having a rear face and a front face, said front face having a substantially circular shape and truncated longitudinally extending side portions, wherein the ratio of the diameter of said front face of said transducer element in the longitudinal direction divided by the diameter in a direction perpendicular thereto is in the range of 1 to 2, said front face defining a surface area for emitting ultrasound waves focused at a focus for effecting said therapeutic treatment;

said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element;

inserting said probe into said body cavity near said body zone to be treated with said front face of said piezoelectric transducer element in front of said body zone to be treated, said focus being located in said body zone; and causing said piezoelectric transducer element to emit ultrasound waves effective for said therapeutic treatment at said focus in said body zone.

69. A method for treating a body zone located inside the body of a patient, comprising the steps of:

providing a probe for insertion in a body cavity near said body zone of said patient, said probe including at least one piezoelectric transducer element operative to emit ultrasound waves at a focus effective for therapeutic treatment of body tissue and having a predetermined maximum cross-sectional perimeter, said piezoelectric transducer element having a rear face and a front face, said front face defining a surface area for emitting ultrasound waves focused at a focus for effecting said therapeutic treatment, and further including a probe support member having a proximal end and a distal end and defining a longitudinal axis, said piezoelectric transducer element having an acoustic window therein and being mounted on said probe support member at the distal end thereof, said distal end of said probe support member having a maximum cross-sectional perimeter conforming closely to said maximum cross-sectional perimeter of said piezoelectric transducer element for facilitating insertion of said probe in said body cavity and maximizing the surface area of said front face of said piezoelectric transducer element;

providing an imaging endo-cavitary probe secured to said probe support member and positioning said endo-cavitary probe beneath said acoustic window for generating an image of said focus for monitoring said therapeutic treatment;

inserting said probe into said body cavity near said body zone to be treated with said front face of said piezoelectric transducer element in front of said body zone to be treated, said focus being located in said body zone; and causing said piezoelectric transducer element to emit ultrasound waves effective for said therapeutic treatment at said focus in said body zone.

* * * * *